United States Patent [19]

Hudson et al.

[11] Patent Number: 4,474,948

[45] Date of Patent: Oct. 2, 1984

[54] BENZAZOLIDES AND THEIR EMPLOYMENT IN PHOSPHITE ESTER OLIGONUCLEOTIDE SYNTHESIS PROCESSES

[75] Inventors: Derek Hudson; Ronald M. Cook, both of San Rafael, Calif.

[73] Assignee: Biosearch, San Rafael, Calif.

[21] Appl. No.: 366,538

[22] Filed: Apr. 8, 1982

[51] Int. Cl.$^3$ ............... C07H 19/18; C07H 19/20
[52] U.S. Cl. ............................... 536/27; 536/28; 536/29
[58] Field of Search .................. 536/27, 28, 29

[56] References Cited

U.S. PATENT DOCUMENTS 3,986,967 10/1976 Okorodudu .................. 548/111
4,174,285 11/1979 Braid ............................. 548/259

FOREIGN PATENT DOCUMENTS 035719 9/1981 European Pat. Off. .

OTHER PUBLICATIONS

Cole, B. H., "Making Genes with Machines", *High Technology,* vol. 1, No. 1, 60–68.
Ogilvie, K. K. et al., *Can. J. Chem.,* 58, 1389, 2686, (1980).
Ogilvie, K. K. et al., *Tetrahedron Letters* 21, 4159, (1980).
Caruthers, M. H. et al., *Nucl. Acids Res.,* Symposium Series #7, 215, (1980).
Beaucage, S. L. et al., *Tetrahedron Letters,* 22, 1859, (1981).

*Primary Examiner*—Johnnie R. Brown
*Assistant Examiner*—Elli Peseler
*Attorney, Agent, or Firm*—Ciotti & Murashige

[57] ABSTRACT

Benzotriazoles are employed in phosphite triester oligonucleotide synthesis. The benzotriazoles also form phosphinedibenzazolides. Processes employing these reagents are also disclosed.

13 Claims, 1 Drawing Figure

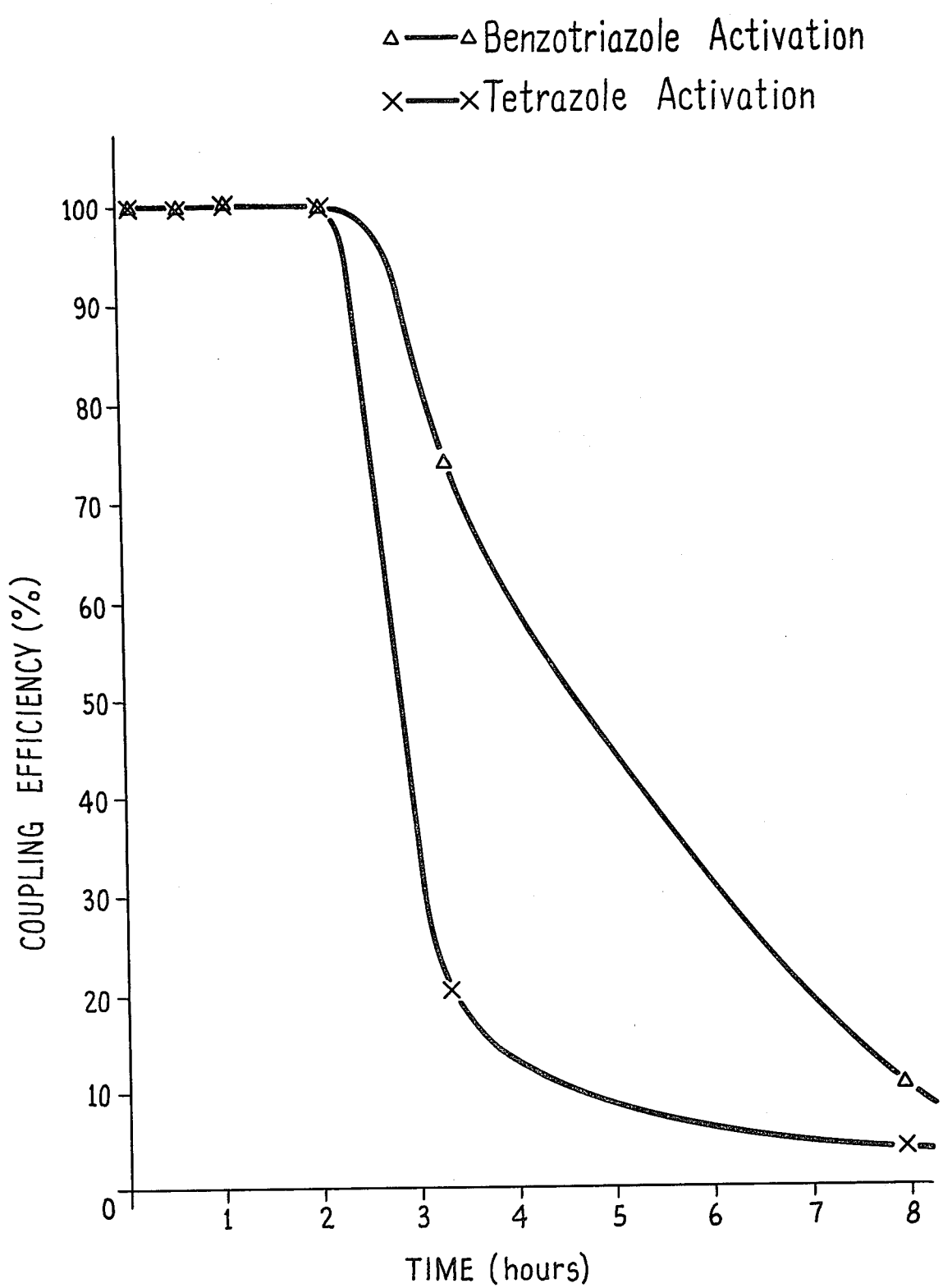

BENZAZOLIDES AND THEIR EMPLOYMENT IN PHOSPHITE ESTER OLIGONUCLEOTIDE SYNTHESIS PROCESSES

TECHNICAL FIELD

This invention is in the field of oligonucleotide synthesis. More particularly, it concerns a group of benzazoles and corresponding benzazolides and their use as activators in phosphate triester oligonucleotide synthesis schemes.

THE PRIOR ART

An article "Making Genes With Machines" by B. H. Cole, appearing in *High Technology*, Vol. 1, No. 1, pages 60–68 provides a general overview of three fundamental processes presently of interest in the fabrication of oligonucleotides in precisely defined sequences. These three processes are known as the phosphate diester process, the phosphate triester process and the phosphite triester process.

The "phosphite triester" process generally involves reaction of a suitably protected nucleoside, a phosphitylating reagent (for example, methoxydichlorophosphine) and a second protected nucleoside that optionally is immobilized on a solid support, followed by mild oxidation. (This general process for oligonucleotide synthesis is described in K. K. Ogilvie, et al *Can. J. Chem.*. 58, 1389 (1980) and 58, 2686 (1980) and *Tetrahedron Letters*, 21, 4159 (1980); as well as M. H. Caruthers, et al *Nucl. Acids Res. Symposium Series* #7, 215 (1980), S. L. Beaucage, et al, *Tetrahedron Letters*, 22, 1859 (1981), and European Patent Application No. 035,719 (16,09,81) all of which for brevity are incorporated herein by reference.

These references teach that it is advantageous to add a mild acid activator to the reactions and that benzimidizole or more commonly 1-H-tetrazole can be employed in this role. In working with both of these systems for nucleotide oligomerization certain fundamental shortcomings related to the art-taught tetrazole activators become apparent. For one, tetrazole is only marginally soluble in usual reaction solvents. This tendency of tetrazole to crystallize causes undesirable dilution and poses risks of clogging the microscale equipment usually employed. For another, simple triazoles and tetrazole cannot be easily modified to enhance their solubility, reactivity and/or stability so that less than optimum life of very expensive reagents is observed and/or less than complete reaction often takes place. This latter failing is very serious in a multi-step oligonucleotide synthesis where usually acceptable conversion losses quickly multiply to given an unreasonable result. It is an object of this invention to provide an advanced and improved family of activators for the phosphite triester oligonucleotide syntheses.

STATEMENT OF THE INVENTION

It has now been found that benzotriazoles of the formula

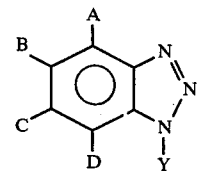

wherein Y is H or an acidic leaving group and A, B, C and D are each independently selected from hydrogen and aromatic ring substituent groups, give superior results as activators in the phosphite triester oligonucleotide preparation route.

These benzotriazoles or the corresponding benzimidazoles can also form phosphinedibenzazolides of the formula

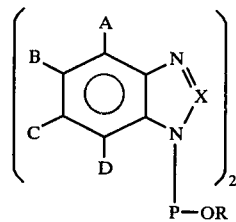

wherein X is N or CH and R is a phosphite protecting group which themselves react to form benzazolides. The materials function as activators in the phosphite triester synthesis schemes. The benzotriazoles form new benzotriazolide intermediates with protected deoxynucleosides and deoxynucleotides. These intermediates have the formula

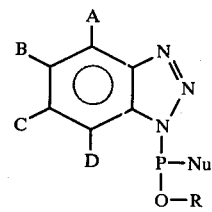

wherein A, B, C and D and X are as previously defined, R is a phosphite protecting group and Nu is a nucleoside, a nucleotide or an oligonucleotide (all with or without protecting groups).

In other aspects, this invention relates to improved phosphite triester oligonucleotide preparation processes employing the subject benzotriazoles or derivatives thereof and, alternatively, the phosphinedibenzazolides.

BRIEF DESCRIPTION OF THE DRAWING

This invention will be described with reference to the drawing wherein FIG. 1 is a graph comparing the coupling efficiency with time of a oligonucleotide-forming reagent when activated by either a compound of this invention or by a material of the prior art.

DETAILED DESCRIPTION OF THE INVENTION

The benzotriazoles employed in this invention, have the structure

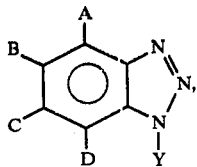

wherein Y is H or an acidic leaving group. In both cases the aromatic rings contain A, B, C and D groups on their 5, 6, 7 and 8 carbons. These may all be hydrogens or they may independently each be aromatic ring-substituenting groups known to the art of organic chemistry. The ability to make these substitutions is one of the major advantages of the present invention as it permits the solubility and reactivity/stability of the materials to be finely tuned. The substituents placed on the ring should be chemically inert under the reaction conditions encountered in oligonucleotide syntheses. Examples of suitable ring-substituenting groups include halogens, such as chloro, bromo, iodo or fluoro; lower alkyls of 1 to 4 carbons such as methyl, ethyl, propyl or the like; simple substituted alkyls such as chloromethyl, trifluoroethyl, and the like; aromatics and substituted aromatics such as benzyl, phenyl, and substituted benzyl or phenyl; lower alkoxies of 1 to 4 carbons such as methoxy, ethoxy, and n and isopropoxy; nitro, nitroso, sulfonato, amino and cyano.

As previously mentioned, the exact A, B, C and D's employed will be at least in part dictated by the properties sought. For example, when a less polar reaction medium is being employed it will often be of advantage to add relatively non-polar A, B, C and D groups, such as the lower alkyls and aromatics, to enhance solubility. Similarly, with these phosphite activating agents, it is believed that, to at least an extent, reactivity is a function of the electronegativity of the nitrogen to which H is attached such that the more "acidic" this proton the more effective the compound is as an activating agent. Conversely, the less "acidic" this proton is, the more stable the system. Thus, by adding electron-donating or withdrawing groups such as F, $NO_2$, $C(CH_3)_3OCH_3$ (alkoxy) and the like to A, B, C or D positions, the system's reactivity/stability can be tailored.

Preferred groups, because of their ready synthesis, include those having each of A, B, C and D as hydrogens, and those having at their "5" carbon (that is, as A) Cl, Br, $NO_2$, $CH_3$, or $O—CH_3$. Other A, B, C and D substituents may be employed, as well, if desired.

These benzotriazole materials react with nucleotides protected nucleotides to give new compounds of the formula

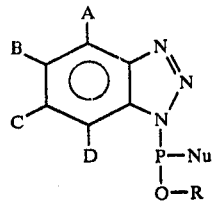

wherein A, B, C, D and X are as previously defined, R may be hydrogen but usually is a suitable base-liable phosphite protecting group. This protecting group is an organic group such as a simple aliphatic or aromatic group, for example, a 1 to 4 carbon lower alkyl or a substituted or unsubstituted aromatic (6 to 12 carbon aryl, alkaryl or aralkyl) such as phenyl, 2-chlorophenyl, 2-methylphenyl, 2-bromophenyl, 4-chlorophenyl, 2,4-dichlorophenyl or the like. Other phosphite triester blocking groups taught by the art to be equivalent may be used as well. Nu is a nucleoside, nucleotide or oligonucleotide particularly one having its "5" hydroxyl and, if appropriate, its base protected. It should be noted that the symbol "Nu" and the term "nucleoside" are defined to include deoxynucleosides and likewise the term "nucleotide" includes deoxynucleotides as these are the materials usually of most interest. Thus, these intermediates can be represented (with deoxy materials) by the formulae I and II.

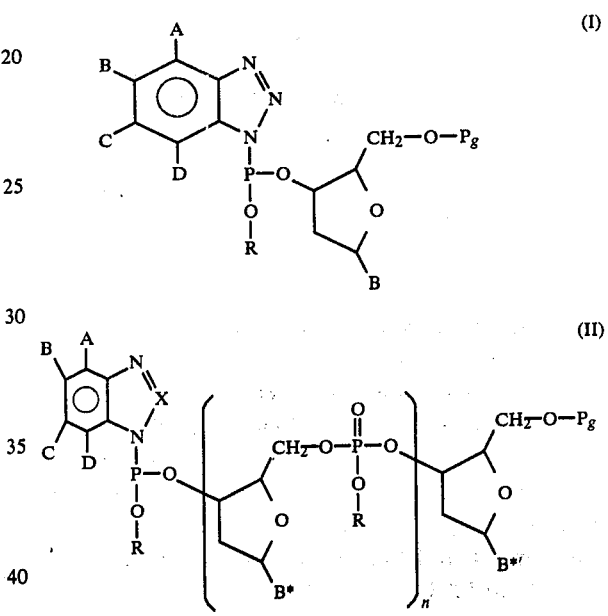

wherein A, B, C, D, X and R are as previously described. $P_g$ is a selectively removable protecting group for the nucleoside's '5 carbon hydroxyl, such as levulinyl and (most commonly) acid labile groups like trityl (triphenylmethyl) and DMT (4,4-dimethoxytrityl). B* and B*' are each bases selected from 1-thyminyl, 1-(N-protected)cytosinyl, 9-(N-protected)adeninyl or 9-(N-protected)guaninyl. The N-protecting groups are materials known in the art and typically include benzoyl groups, isobutyryl groups and anisoyl groups with the benzoyl group being the group of choice with adenine and cytosine and isobutyryl being the group of choice with guanine, and n is an integer, usually 1 but also higher numbers such as 2,3,4,5 up to 10 or 12 or more, if desired. In these higher mer unit materials B* will be selected independently in each repeat unit. It will also be appreciated that nucleosides and nucleotides can simply replace the deoxy materials shown here.

These activated species may be prepared by reacting an optionally protected nucleoside phosphite (or, as particularly shown, phosphoramidite) and the benzotriazole such as

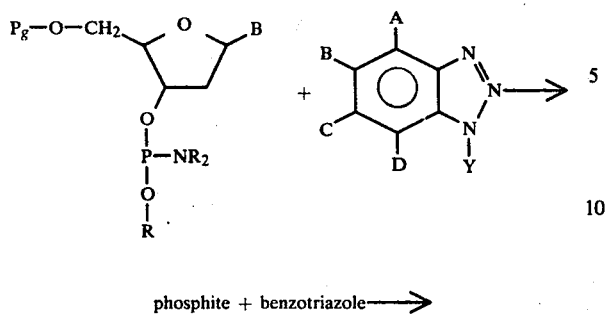

phosphite + benzotriazole ⟶

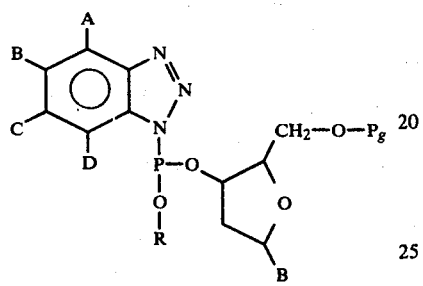

activated species.

This reaction may be carried out in solution in a suitable organic aprotic reaction solvent such as acetonitrile, pyridine, tetrahydrofuran, dimethylformamide, 1,4-dioxan, methylene chloride, chloroform, ethyl acetate, acetone, diethyl ether, benzene and mixtures thereof. A substantial (2 to 20 times) molar excess of the benzotriazole is usually used. This reaction is rapid and is usually complete in 1 to 20 minutes at temperatures from −20° C. to 50° C.

These active species can be used as building blocks in the growth of oligonucleotides. For instance they can be used to couple to a second nucleoside that has been attached through its 3' hydroxyl group to a solid support, denominated $S_s$ in the following formula

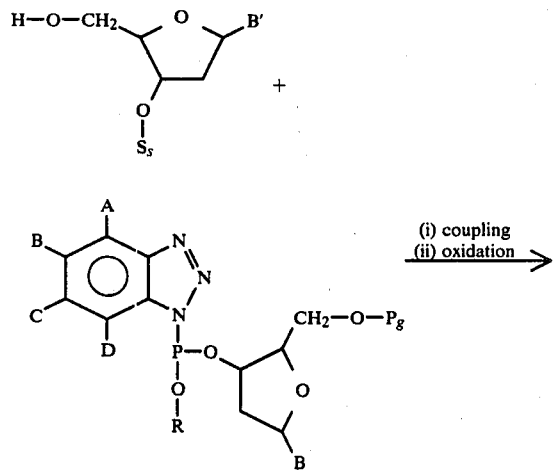

-continued

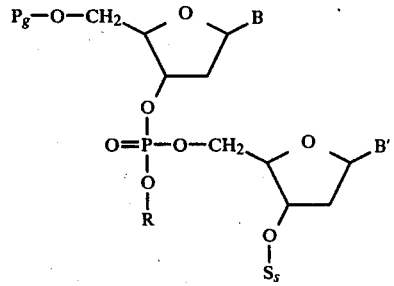

In the subsequent oxidation step, iodine or a similarly effective oxidation agent, e.g. hydrogen peroxide or alkyl or arylperoxides or peroxyacids, such as m-chloroperbenzoic acid, can be used. This product can have its 5' hydroxyl deblocked and be further reacted with additional active species to add yet further nucleotide units. Thereafter the entire oligonucleotide is removed from the support, the bases are unblocked and the phosphate protecting group can be removed.

Alternatively, the nucleoside benzazolide can be prepared by reaction of a nucleoside with the corresponding phosphineditriazolide or diimidazolide, that is

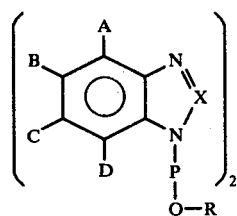

wherein A, B, C and D and X are as previously defined and R is a phosphite protecting group as previously described.

The dibenzotriazolides and dibenzoimidazolides can be formed by reaction of the benzazole with a dihalogen-substituted oxy-phosphorus compound such as phosphorodichloridite, e.g., p-chlorophenylphosphorodichloridite or the like.

-continued

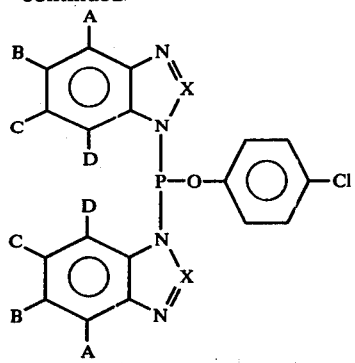

Other organo groups can replace the chlorophenyl groups—for example, lower alkyls of 1 to 4 carbons and aryls of 6 or 10 carbons all with optional substituents such as halo's, alkyls, so too other halogens can replace the chloros attached to the phosphorous.

The reaction is typically carried out for from 10 to 30 minutes at low temperature (e.g., −70° C. to +10° C.) in an organic solvent such as pyridine, dioxan, tetrahydrofuran, acetonitrile, chloroform or the like, in the presence of an excess of the benzazole or optionally a suitable organic base, particularly an organic testing amine especially pyridine or a substituted pyridine such as collidine or lutidine.

The in situ-generated dibenzazolide intermediate is generally used without isolation. It is firstly reacted with a 5' protected derivative to give a monobenzazolide, which is further reacted with a hydroxyl component HOR'.

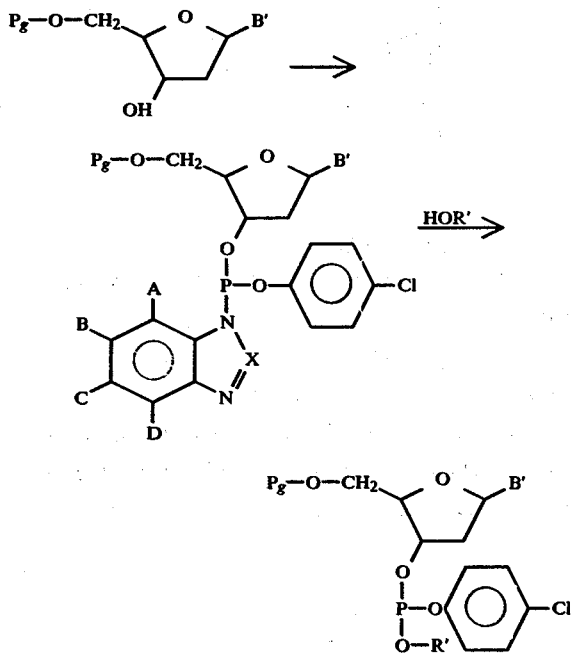

When HOR' is a 5' or 3' protected nucleotide either in solution or attached to a solid support, an internucleotide bond is generated without recourse to an external coupling reagent. Subsequent oxidation with an oxidizing agent as previously described gives the protected phosphate-nucleotide bond.

The materials of this invention and their use in the two oligonucleotide synthesis techniques are further illustrated by the following Examples. These are presented to illustrate the invention and are not intended to limit the invention's scope.

EXAMPLE I

Use of Benzazoles as Activators in Phosphite Triester Synthesis and Comparison with 1-H Tetrazole N-Benzoylcytidine linked from the 3' hydroxyl group via a hemisuccinate bridge to aminopropyl-substituted HPLC-grade silica (Vydac) was used as the solid-phase support. Samples (100 mg each; 10 micromoles) were shaken in sealed test tubes in acetonitrile (1 ml) with each of the four 5'-dimethoxytrityl-deoxynucleoside-3'-dimethylaminophosphoramidites and either tetrazole (1 mmole) or benzotriazole (600 micromoles) to form the tetrazolide or benzotriazolide-phosphite active species, the latter being a compound of this invention. After thorough washing by repeated centrifugation and subsequent decanting, and oxidation with 0.01M iodine, the support was treated with 2.75% (w/v) trichloroacetic acid in methylene chloride (10 ml) for 5 minutes. Spectrophotometric assay of the dimethoxytrityl carbonium ion produced in the supernatant demonstrated that all couplings had proceeded to greater than 95% of theoretical yield.

This test system was also used to show that 5-nitro- and 5-chloro-1,2,3-benzotriazole were as efficient amidite activators as tetrazole and unsubstituted benzotriazole. Additionally, using this method and a 30-fold excess of the corresponding G-amidite, it was shown that solutions activated with 1,2,3-benzotriazole gave efficient coupling up to 3 hours after their preparation at room temperature, whereas at the corresponding stage tetrazole-activated solutions gave 20% coupling yields. (See FIG. 1 where this is shown graphically.)

EXAMPLE II

Syntheses of Test Deoxynucleotide 5'GTTAAC3'

The syntheses were performed using a BIOSEARCH Synthesis Automation Module (SAM 1) consisting of a microprocessor-controlled array of solenoid-actuated valves sampling reagents and solvents which were pumped through N-benzoyl-cytidine-substituted Vydac (150 mg) packed in a Whatman guard column. Mixing of amidites with benzotriazole wre performed in-line. The basic synthesis program used consisted of: (i) CH$_3$CN (4 min, 4 ml/min); (ii) 2.75% (w/v) trichloroacetic acid in methylene chloride (5 min, 2.5 ml/min); (iii) CH$_3$CN wash (2 min, 4 ml/min); (iv) DMT-nucleoside-phosphoramidite (10 equivalents) in acetonitrile (2.5 ml) and benzotriazole (60 equivalents) in acetonitrile (2.5 ml) sampled alternately at 0.5 second intervals at an overall flow rate of 0.5 ml/min for 10 minutes; (v) CH$_3$CN wash (2 min, 4 ml/min); (vi) oxidation with 0.01M iodine in 40% (v/v) THF/water (3 min, 2.5 ml/min); (vii) CH$_3$CN wash (2 min, 4 ml/min); and (viii) 0.5M solution of a mixture of equivalent amounts of acetic anhydride and dimethylaminopyridine in THF (5 min, 1 ml/min). On completion of the five addition cycles a trichloroacetic acid treatment and a final wash step were performed. The support was unpacked and treated with concentrated ammonia for 1 day at room temperature. The supernatant was heated at 50° for one day and the ammonia evaporated. The residue was dissolved in water (5 ml) and a portion (0.25 ml) purified on a calibrated Whatman SAX column eluted at 2 ml/min with a gradient over 30 minutes from 0.03M to 0.3M potassium phosphate buffer (pH 6.1) containing 20% (v/v) acetonitrile. The main peak, eluting after 10 ml, was collected, desalted and shown by standard methods to be the desired homogeneous hexanucleotide isolated in 33% overall yield based on the original level of substitution of the Vydac support. In a second synthesis using tetrazole activation under similar conditions, a 25% yield of identical product was obtained.

EXAMPLE III

Preparation and Use of Methoxyphosphine Dibenzotriazolide

A 0.5M solution of methoxyphosphine dibenzotriazolide was prepared by the addition at −20° of a solution of methyl-phosphorodichloridite (1.01 ml) in THF (9 ml) to a solution of benzotriazole (4.76 g, 50 mmoles) and pyridine (2 ml) made up to 10 ml with THF. After 15 minutes the solution was cooled to −60° and aliquots (0.9 equivalents) added to 0.18M solutions of the DMT-nucleosides in THF. Synthesis of GTTAAC was performed in a manner similar to that described in Example II. The isolated nucleotide (30% yield) was identical to that obtained in Example II.

We claim:

1. A benzotriazolide of the formula

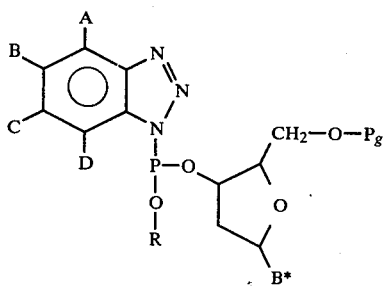

wherein A, B, C, and D are independently selected from among hydrogen, chloro, bromo, iodo, fluoro, lower alkyls of 1 to 4 carbon atoms, substituted lower alkyls, benzyl, phenyl, substituted benzyl, substituted phenyl, lower alkoxies of 1 to 4 carbon atoms, nitro, nitroso, sulfonato amino and cyano, R is hydrogen or a base labile phosphite protecting group, $P_g$ is a selectively removable protecting group selected from levulinyl and acid labile protecting groups and B* is a base selected from 1-thyminyl, 1-(N-protected)cytosinyl, 9-(N-protected)adeninyl and 9-(N-protected)guaninyl.

2. The benzotriazolide of claim 1 wherein B, C and D are hydrogens.

3. The benzotriazolide of claim 2 wherein R is a base labile phosphite protecting group.

4. The benzotriazolide of claim 3 wherein R is selected from among 1 to 4 carbon alkyls, 6 to 12 carbon aryls, alkaryls and aralkyls and halo-substituted 6 to 12 carbon aryls, alkaryls and aralkyls.

5. The benzotriazolide of claim 1 wherein the N-protected base is protected with a group selected from among benzoyl, isobutyrl and anisoyl.

6. A phosphitylated oligonucleotide of the formula:

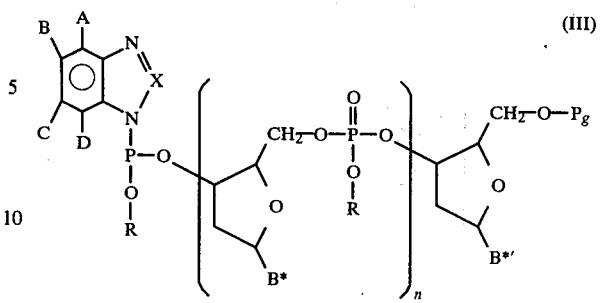

wherein X is N or CH, A, B, C and D are each selected from hydrogen and chloro, bromo, iodo, fluoro, lower alkyls of 1 to 4 carbon atoms, substituted lower alkyls, benzyl, phenyl, substituted benzyl, substituted phenyl, lower alkoxies of 1 to 4 carbon atoms, nitro, nitroso, sulonato amino and cyano, R is a base labile phosphite protecting group, $P_g$ is a protecting group selected from levulinyl and acid-labile protecting groups and B* and B*' are independently selected from 1-thyminyl, 1-(N-protected)cytosinyl, 9-(N-protected)adeninyl and 9-(N-protected)guaninyl, and n is an integer 1 or greater.

7. In a process of oligonucleotide synthesis wherein a first nucleoside optionally affixed to a solid support is reacted with a phosphitylated second nucleoside or nucleotide under nucleotide coupling conditions in the presence of an activating agent, the improvement comprising employing as said activating agent a benzotriazole of the formula

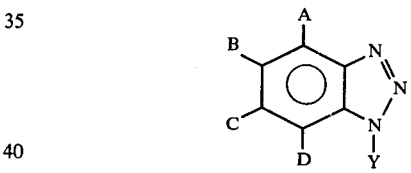

wherein A, B, C and D are independently selected from among hydrogen and chloro, bromo, iodo, fluoro, lower alkyls of 1 to 4 carbon atoms, substituted lower alkyls, benzyl, phenyl, substituted benzyl, substituted phenyl, lower alkoxies of 1 to 4 carbon atoms, nitro, nitroso, sulfonato amino and cyano, and Y is hydrogen or a leaving group.

8. The process of claim 7 being further characterized as a flow process in which the first nucleotide is affixed to a solid support in a reaction zone and controlled amounts of solutions of said second nucleoside or nucleotide and said activating agent are serially fed for controlled periods into said reaction zone for a reaction period.

9. The process of claim 8 wherein the controlled periods are for from 50 microseconds to 5 seconds and the reaction period is at least 50 times a controlled period.

10. The process of claim 9 being further characterized as a flow process in which the first nucleotide is affixed to a solid support and controlled amounts of solutions of said second nucleoside or nucleotide and said activating agent are passed over said solid support immediately after being admixed together.

11. A process for synthesizing an oligonucleotide comprising (a) reacting a nucleotide or nucleoside with a phosphinedibenzazolide of the formula

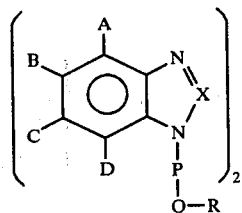

wherein X is N or CH, A, B, C and D are independently selected from hydrogen and chloro, bromo, iodo, fluoro, lower alkyls of 1 to 4 carbon atoms, substituted lower alkyls, benzyl, phenyl, substituted benzyl, substituted phenyl, lower alkoxies of 1 to 4 carbon atoms, nitro, nitroso, sulfonato amino and cyano, and R is a base-labile phosphite-protecting group, to yield a phosphitylated nucleotide, and (b) coupling said phosphitylated nucleotide with a second nucleotide or nucleoside.

12. A process for synthesizing an oligonucleotide of claim 11 wherein X is N.

13. A process for synthesizing an oligonucleotide of claim 11 wherein X is CH.

* * * * *